(12) United States Patent
Luque Vera et al.

(10) Patent No.: US 10,016,523 B2
(45) Date of Patent: Jul. 10, 2018

(54) DEVICE FOR THE DIFFUSION OF VOLATILE SUBSTANCES

(71) Applicant: Zobele España, S.A., Barcelona (ES)

(72) Inventors: Sergio Luque Vera, Barcelona (ES); Ruben Garcia Fabrega, Barcelona (ES)

(73) Assignee: Zobele España, S.A., Barcelona (ES)

( * ) Notice: Subject to any disclaimer, the term of this patent is extended or adjusted under 35 U.S.C. 154(b) by 0 days.

(21) Appl. No.: 15/109,137

(22) PCT Filed: Dec. 26, 2014

(86) PCT No.: PCT/ES2014/070978
§ 371 (c)(1),
(2) Date: Jun. 30, 2016

(87) PCT Pub. No.: WO2015/101689
PCT Pub. Date: Jul. 9, 2015

(65) Prior Publication Data
US 2016/0325003 A1    Nov. 10, 2016

(30) Foreign Application Priority Data
Dec. 30, 2013 (ES) .................. 201331931

(51) Int. Cl.
| | | |
|---|---|---|
| *A61L 9/12* | (2006.01) | |
| *B01F 3/04* | (2006.01) | |
| *A01M 1/20* | (2006.01) | |
| *H01L 41/09* | (2006.01) | |

(52) U.S. Cl.
CPC .............. *A61L 9/127* (2013.01); *A01M 1/205* (2013.01); *A01M 1/2033* (2013.01); *A61L 9/122* (2013.01); *B01F 3/0407* (2013.01); *A61L 2209/132* (2013.01); *H01L 41/094* (2013.01)

(58) Field of Classification Search
CPC ........... B01F 3/04; B01F 3/0407; A61L 9/122
USPC .............................. 261/81, DIG. 88; 239/302
See application file for complete search history.

(56) References Cited

U.S. PATENT DOCUMENTS

| | | | |
|---|---|---|---|
| 2005/0279854 A1 | 12/2005 | Martens, III et al. | |
| 2013/0026250 A1* | 1/2013 | Burt ................ | A01M 1/205 239/302 |

FOREIGN PATENT DOCUMENTS

| | | | | |
|---|---|---|---|---|
| EP | 1509081 | | 3/2005 | |
| GB | 2299861 A | * | 10/1996 | ............ G01P 15/097 |
| JP | 05-009553 | | 2/1993 | |
| JP | 2002-130199 | | 5/2002 | |
| JP | 2002-209500 | | 7/2002 | |

(Continued)

OTHER PUBLICATIONS

Supplementary European Search Report and the European Search Opinion dated Aug. 8, 2017 From the European Patent Office Re. Application No. 14876569.6. (7 Pages).

(Continued)

*Primary Examiner* — Robert A Hopkins

(57) ABSTRACT

The device for diffusing volatile substances comprises means for generating an air stream, and is characterized in that said means for generating an air stream comprise a flexible sheet (1) and at least one piezoelectric element (2), such that said piezoelectric element (2) causes said flexible sheet (1) to expand and shrink to generate the air stream.
It allows generating an air flow that is adapted to the geometry of the evaporation surface.

14 Claims, 3 Drawing Sheets

(56) References Cited

FOREIGN PATENT DOCUMENTS

| JP | 2006-105536 | 4/2006 |
| JP | 2009-112173 | 5/2009 |
| JP | 2011-144743 | 7/2011 |
| WO | WO 03/103387 | 12/2003 |
| WO | WO 2015/101689 | 7/2015 |

OTHER PUBLICATIONS

International Search Report and the Written Opinion dated Feb. 20, 2015 From the Oficina Espanola de Patentes y Marcas Re. Application No. PCT/ES2014/070978 and Its Translation Into English.

* cited by examiner

DEVICE FOR THE DIFFUSION OF VOLATILE SUBSTANCES

RELATED APPLICATIONS

This application is a National Phase of PCT Patent Application No. PCT/ES2014/070978 having International filing date of Dec. 26, 2014, which claims the benefit of priority of Spanish Patent Application No. P201331931 filed on Dec. 30, 2013. The contents of the above applications are all incorporated by reference as if fully set forth herein in their entirety.

The present invention relates to a device for diffusing volatile substances, particularly to a device in which one or more volatile substances is diffused by means of an air flow having a non-cylindrical geometry.

BACKGROUND OF THE INVENTION

Electric devices, which are powered by battery cells, batteries or the power grid, diffusing volatile substances by means of generating an air stream through a blade fan, are known.

This type of device is usually designed to increase efficacy and achieve optimal user control of the dispensing or evaporation level.

This type of device is designed to improve evaporation and/or diffusion of the volatile substances with the aid of an additional air flow, even without temperature constraints.

These devices, however, have a series of drawbacks that are indicated below.

On one hand, most of the earlier solutions have high or very high power consumption, so sometimes they can barely be made to work with batteries, and if they do, the duration of said batteries is very limited.

On the other hand, with known fan devices, the generated air flow has a cylindrical geometry, which does not coincide with most elements for diffusing volatile substances, which usually have a rectangular projection.

Furthermore, within this cylindrical geometry, the highest air speed is in the outermost area of the perimeter, which usually does not coincide with the element for diffusing the volatile substance. This means that a significant part of the air flow is wasted, which again means a loss in energy efficiency.

In addition, the noise coming from earlier solutions may not be negligible and can even increase over time. This can eventually come to represent an annoyance for the user.

Another important point in some of the earlier solutions is the size and shape they adopt, usually being quite bulky, making it necessary to design an electric diffuser of a considerable size.

Therefore, the need for a device for diffusing volatile substances solving the aforementioned drawbacks is evident.

SUMMARY OF THE INVENTION

The aforementioned drawbacks are solved with the device for diffusing volatile substances of the invention, having other advantages that will be described below.

The device for diffusing volatile substances according to the present invention comprises means for generating an air stream and is characterized in that said means for generating an air stream comprise a flexible sheet and at least one piezoelectric element, such that when said piezoelectric element is subjected to expansion and shrinkage, it causes said flexible sheet to move back and forth to generate the air stream.

According to an alternative embodiment, said means for generating an air stream comprise two piezoelectric elements, said piezoelectric elements being placed on opposite faces of said flexible sheet.

Advantageously, the device for diffusing volatile substances according to the present invention also comprises a container of volatile substances defining an evaporation surface, and in which the end of said flexible sheet generating the air stream is oriented towards said evaporation surface.

The width of said end of said flexible sheet generating the air stream preferably coincides with the width of said evaporation surface. If the evaporation surface is a wick, said width of the flexible sheet can coincide with the diameter of the wick.

Furthermore, said flexible sheet can preferably be rectangular or quadrangular.

According to an optional embodiment, said means for generating an air stream are housed in a casing, said casing being provided with air inlet openings and outlet openings.

The device for diffusing volatile substances according to the present invention provides at least the following advantages:

- It allows generating air flow that is adapted to the geometry of the evaporation surface.
- Power consumption is lower than in conventional devices, which means that, in the event of using batteries, the duration thereof is longer than in conventional devices.
- The dimensions and operation of the device according to the present invention means that there can be different air flows (and therefore different evaporations) depending on the position in which the flexible sheet is located with respect to the volatile substance to be evaporated.
- The noise is virtually negligible throughout the service life of the product, since there is no friction or wear in the materials.
- The air flow can be regulated by means of modifying the voltage amplitude, but also by modifying the frequency of the alternating signal generated.
- Evaporation can be controlled and adjusted also by means of casings, opening and closing the air inlet and/or outlet depending on the desired air flow.
- The size of the device according to the present invention can be configured and adjusted according to the application,
- Optionally, should the system to be evaporated require it, several devices could be used together.

BRIEF DESCRIPTION OF THE SEVERAL VIEWS OF THE DRAWINGS

To better understand the preceding description, several drawings are attached in which a practical embodiment is depicted schematically and only by way of non-limiting example.

DESCRIPTION OF SPECIFIC EMBODIMENTS OF THE INVENTION

Figure 1:
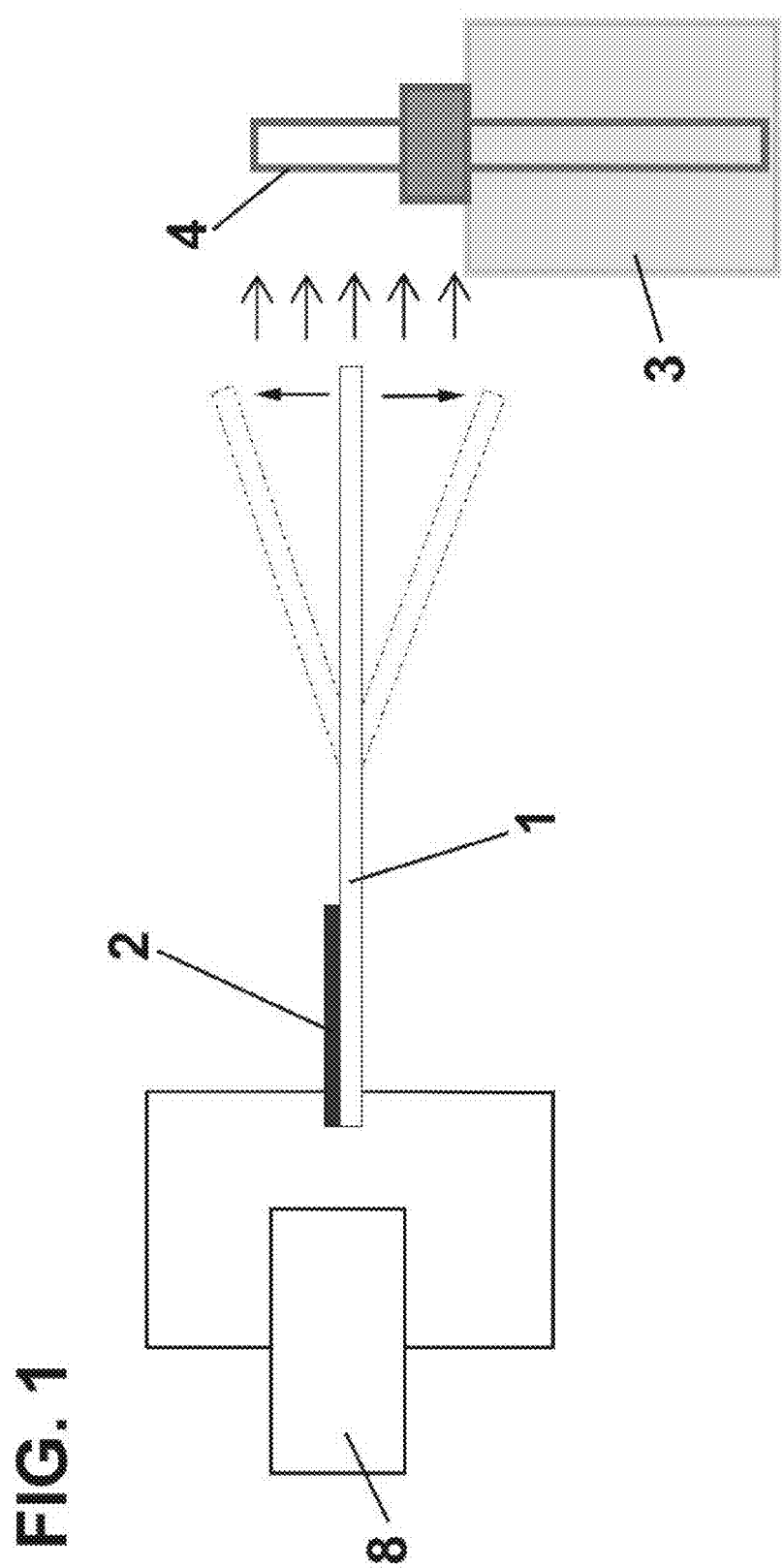
FIG. 1 is a schematic elevational view of the device for diffusing volatile substances according to the present invention, according to a first preferred embodiment.

According to the embodiment shown in FIG. 1, the device of the present invention comprises means for generating air flow, comprising a flexible sheet 1 and a piezoelectric element 2. Said flexible sheet 1 is preferably rectangular or quadrangular, or could have any suitable shape. For example, it could have a curved part if required for any reason.

Said piezoelectric element 2 is connected to an electric power supply 8, such that when an AC voltage is applied to said piezoelectric element 2, the latter expands and shrinks.

This causes the sheet 1 to bend and move back and forth at the same frequency as the applied voltage. This back and forth movement causes an air flow that can be used to help with and/or improve evaporation and/or diffusion of organic volatile substances.

In the event that the electric power supply 8 is one or more batteries, an additional, non-depicted circuit is required to generate and amplify the alternating signal required for the operation of the piezoelectric element. In the event that the electric power supply 8 is the power grid, the additional circuit may not be required.

This additional circuit is capable of controlling air flow by modifying the amplitude and/or frequency of the generated signal for feeding the piezoelectric element 8, so evaporation and/or diffusion of the organic volatile substances could be controlled.

FIG. 1 also depicts a container 3 including, among others, the volatile substance to be diffused, said container defining an evaporation surface 4, which in this case can be a wick. In this case, the width of the flexible sheet can coincide with the diameter of the wick, although it could also have a different dimension.

As can be seen in the drawing, the end of said flexible sheet 1 generating the air flow is oriented towards said wick.

Figure 2:
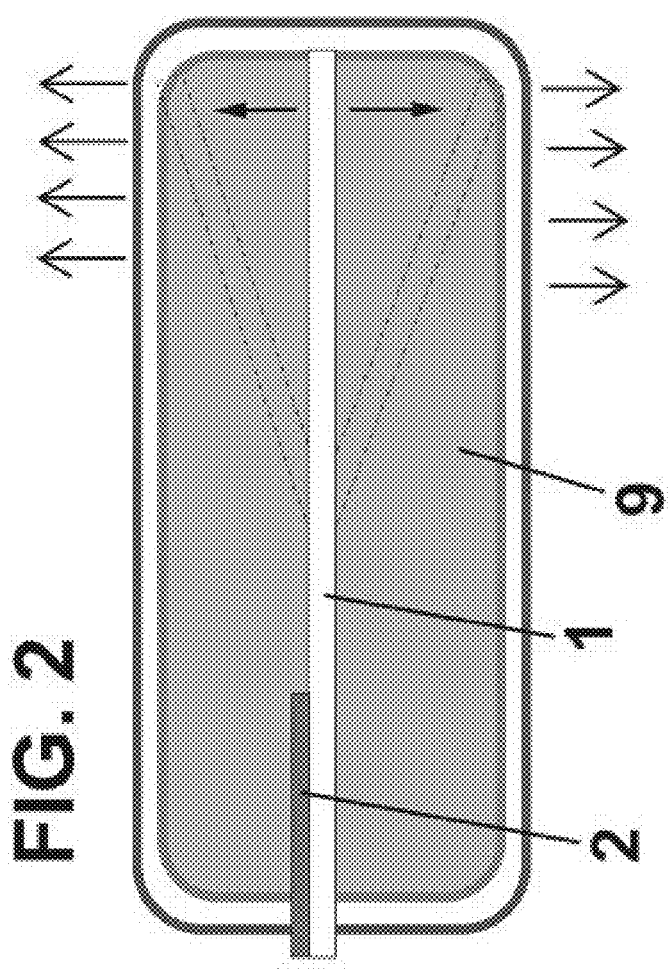
FIG. 2 is a schematic plan view of the device for diffusing volatile substances according to the present invention, according to a second preferred embodiment.

FIG. 2 depicts a second embodiment, in which the flexible sheet 1 is arranged in perpendicular on a membrane 9. In this case, the air flow is confined in a rectangular geometry parallel to the evaporation surface.

Figure 3:
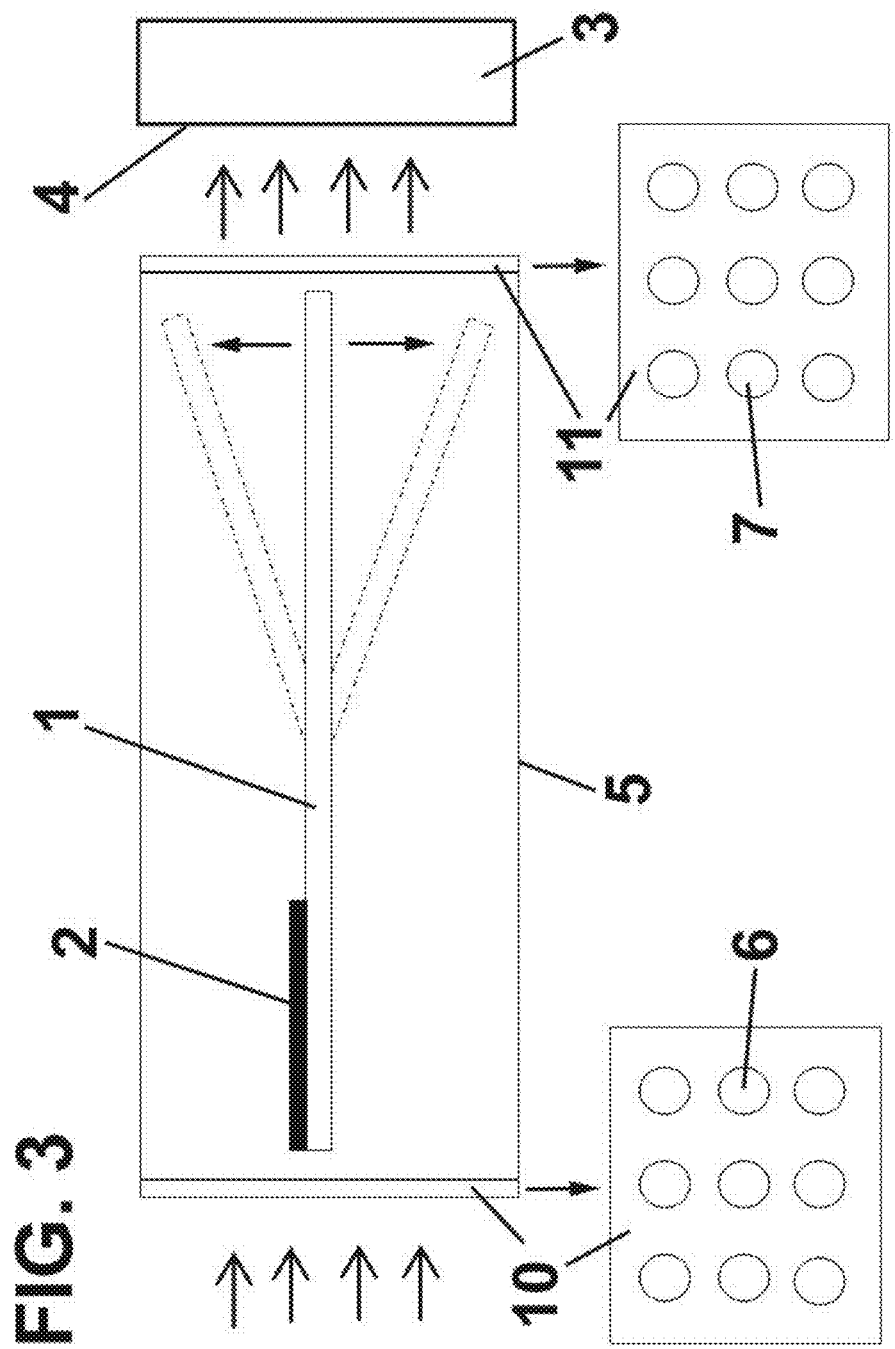
FIG. 3 is a schematic elevational view of the device for diffusing volatile substances according to the present invention, according to a third preferred embodiment.

FIG. 3 depicts a third embodiment, in which the flexible sheet 1 and the piezoelectric element 2 are arranged inside a casing 5.

Said casing 5 is provided with an inlet cover 10 with a plurality of inlet openings 6 and an outlet cover 11 with a plurality of outlet openings 7, such that the air circulates inside said casing 5 due to the action of said flexible sheet 1 when it is operated by said piezoelectric element 2, as described above.

In this case, it can be seen in FIG. 3 that the width of said end of said flexible sheet 1 generating the air stream substantially coincides with the width of said evaporation surface 4.

Though not depicted in the drawings, it should be indicated that the means for generating an air stream could comprise more than one piezoelectric element 2, for example two piezoelectric elements, placed on opposite faces of said flexible sheet 1.

Despite having referred to a specific embodiment of the invention, it is evident for a person skilled in the art that the device for diffusing volatile substances that has been described can be subjected to a number of variations and modifications, and that all the mentioned details can be replaced with other technically equivalent details, without departing from the scope of protection defined by the attached claims.

What is claimed is:

1. Device for diffusing volatile substances, comprising means for generating an air stream, characterized in that said means for generating an air stream comprise an elongated flexible sheet (1) and at least one piezoelectric element (2) attached to said elongated flexible sheet at a proximal longitudinal end of said flexible sheet, such that said piezoelectric element (2) causes said elongated flexible sheet (1) to move in a flapping movement, generating the air stream in an outward direction substantially parallel to a longitudinal axis of said elongated flexible sheet in a middle position;
    wherein said flapping movement, a movement amplitude of said distal end is larger than a movement amplitude of said proximal end.

2. Device for diffusing volatile substances according to claim 1, wherein said means for generating an air stream comprise two piezoelectric elements (2), being placed said piezoelectric elements (2) on opposite faces of said elongated flexible sheet (1).

3. Device for diffusing volatile substances according to claim 1, also comprising a container (3) of volatile substances defining an evaporation surface (4), and wherein the distal end of said elongated flexible sheet (1) generating the air stream is oriented towards said evaporation surface (4) and said generated air stream is directed from said distal end toward said evaporation surface.

4. Device for diffusing volatile substances according to claim 3, wherein the width of said end of said elongated flexible sheet (1) generating the air stream coincides with the width of said evaporation surface (4).

5. Device for diffusing volatile substances according to claim 1, wherein said elongated flexible sheet (1) is substantially rectangular or quadrangular.

6. Device for diffusing volatile substances according to claim 1, wherein said means for generating an air stream are housed in a casing (5), said casing (5) being provided with air inlet openings (6) allowing air to enter said casing through an end adjacent to said proximal end of said elongated flexible sheet, and outlet openings (7) allowing said generated air stream to exit said casing from an end adjacent to said distal end of said elongated flexible sheet.

7. Device for diffusing volatile substances according to claim 2, also comprising a container (3) of volatile substances defining an evaporation surface (4), and wherein the distal end of said elongated flexible sheet (1) generating the air stream is oriented towards said evaporation surface (4) and said generated air stream is directed from said distal end toward said evaporation surface.

8. Device for diffusing volatile substances according to claim 2, wherein said elongated flexible sheet (1) is substantially rectangular or quadrangular.

9. Device for diffusing volatile substances according to claim 3, wherein said elongated flexible sheet (1) is substantially rectangular or quadrangular.

10. Device for diffusing volatile substances according to claim 4, wherein said elongated flexible sheet (1) is substantially rectangular or quadrangular.

11. Device for diffusing volatile substances according to claim 1, wherein said generated air stream is regulated by modifying a voltage amplitude of a signal fed to said at least one piezoelectric element.

12. Device for diffusing volatile substances according to claim 1, wherein said generated air stream is regulated by modifying a frequency of an alternating signal fed to said at least one piezoelectric element.

13. Device for diffusing volatile substances according to claim 6, wherein said generated air stream is controlled by opening and closing of at least one of said air inlet openings and said outlet openings.

14. Device for diffusing volatile substances according to claim 3, wherein a span of the flapping movement of said distal end is substantially similar to a length of said evaporation surface and said flapping movement is parallel to a longitudinal axis of said evaporating surface.

* * * * *